United States Patent [19]
Takata et al.

[11] Patent Number: 5,662,546
[45] Date of Patent: Sep. 2, 1997

[54] METHOD OF POWER TRANSMISSION WITH OPTIMUM TRACTION COEFFICIENT OF DRIVING AND DRIVEN MEMBERS

[75] Inventors: Hirotoshi Takata, Yokohama; Susumu Suzuki, Minami-ashigara, both of Japan

[73] Assignee: NSK Ltd., Tokyo, Japan

[21] Appl. No.: 434,124

[22] Filed: May 2, 1995

Related U.S. Application Data

[63] Continuation of Ser. No. 63,334, May 19, 1993, abandoned.

[30] Foreign Application Priority Data

Jun. 8, 1992 [JP] Japan ..................... 4-171498

[51] Int. Cl.$^6$ .......................... F16H 15/38; F16H 55/32
[52] U.S. Cl. ................................ 476/40; 476/72
[58] Field of Search ........................ 476/40, 72

[56] References Cited

U.S. PATENT DOCUMENTS

| | | |
|---|---|---|
| 4,871,476 | 10/1989 | Yoshimura et al. ............ 252/565 |
| 4,909,092 | 3/1990 | Machida et al. ............... 74/200 |
| 5,344,582 | 9/1994 | Umemoto et al. ............. 252/9 |

FOREIGN PATENT DOCUMENTS

| | | |
|---|---|---|
| 62-71465 | 5/1987 | Japan . |
| 62-270856 | 11/1987 | Japan . |

OTHER PUBLICATIONS

Heilich III et al. *Traction Drives*, pp. 144–167. © 1983, Marcel Dekker, Inc.

*Primary Examiner*—Hoang Nguyen
*Attorney, Agent, or Firm*—Shapiro and Shapiro

[57] ABSTRACT

A power transmission device controlling a contact surface pressure on contact areas between driving surfaces and a driven surface to transmit large power while ensuring a life-span of rolling fatigue. In this device, a traction coefficient $\mu$ expressed by a ratio T/N is maximized, where T is the driving force transmitted from driving members to a driven member, and N is the pressing force acting on the contact areas in perpendicular directions.

1 Claim, 2 Drawing Sheets

METHOD OF POWER TRANSMISSION WITH OPTIMUM TRACTION COEFFICIENT OF DRIVING AND DRIVEN MEMBERS

This is a continuation of application Ser. No. 08/063,334 filed May 19, 1993, now abandoned.

BACKGROUND OF THE INVENTION

1. Field of the Invention

The present invention relates to a power transmission device utilized in the form of a toroidal type continuously variable transmission employed as, e.g., a transmission for an automobile.

2. Related Background Art

There has been pursued the use of a toroidal type continuously variable transmission illustrated in FIGS. 3A and 3B as a transmission for an automobile. In this toroidal type continuously variable transmission, as disclosed in, e.g., Japanese Utility Model Laid-Open Application No. 62-71465, an input-side disk 2 is supported concentrically with an input shaft 1, and an output-side disk 4 is fixed to the end of an output shaft 3. A casing encases the toroidal type continuously variable transmission. A support bracket is provided on the inner surface of the casing or inwardly of this casing. The support bracket is provided with trunnions 5, 5 swinging about a twist position with respect to the input shaft 1 and the output shaft 3.

Each of the trunnions 5, 5 is composed of a metal material exhibiting a sufficient rigidity. Power rollers 7, 7 are rotatably supported on the peripheries of displacement shafts 6, 6 provided at the central parts of the respective trunnions 5, 5. Each of the power rollers 7, 7 is interposed between the input- and output-side disks 2, 4. An input-side concave surface 2a and an output-side concave surface 4a are formed on side surfaces, opposite to each other, of the input- and output-side disks 2, 4 in the axial direction. The concave surfaces 2a, 4a assume circular arcs in section that are formed about the swinging centers of the respective trunnions 5, 5. Then, the input- and ouput-side concave surfaces 2a, 4a are brought into contact with outer peripheral surfaces 7a, 7a of the power rollers 7, 7 that are formed as spherically convex surfaces.

A loading cam type pressure unit 8 is interposed between the input shaft 1 and the input-side disk 2. This pressure unit 8 elastically thrusts the input-side disk 2 toward the output-side disk 4. The pressure unit 8 is constructed of a cam plate 9 rotating together with the input shaft 1 and a plurality of (e.g., four) rollers, 11 held by a retainer 10. A cam surface 12 having concave and convex portions concaved and convexed in the peripheral direction is formed on one surface (right surface in FIGS. 3A and 3B) of the cam plate 9. Further, a similar cam surface 13 is formed on an external surface (left surface in FIGS. 3A and 3B) of the input-side disk 2. Then, the plurality of rollers 11 are rotatable about axes in the radial directions with the input shaft 1 being centered.

When the cam plate 9 rotates with rotation of the input shaft 1, the cam surface 12 presses the plurality of rollers 11 against the cam surface 13 formed on the outer end surface of the input-side disk 2. As a result, the input-side disk 2 is pressed against the plurality of power rollers 7, 7. Simultaneously, the input-side disk 2 rotates when a pair of the cam surfaces 12, 13 engage with the plurality of rollers 11. Subsequently, the rotations of this input-side disk 2 are transmitted via the plurality of power rollers 7, 7 to the output-side disk 4. The output shaft 3 fixed to the output-side disk 4 rotates.

FIG. 3A shows a state of the transmission in which the trunnions 5, 5 are swung to effect a deceleration. In this state, the displacement shafts 6, 6 are tilted so that the outer peripheral surfaces 7a, 7a of the power rollers 7, 7 are each brought into contact with a closer-to-center part of the input-side concave surface 2a and with a closer-to-outer-periphery part of the output-side concave surface 4a. Conversely, when effecting an acceleration, the trunnions 5, 5 are swung as shown in FIG. 3B. The displacement shafts 6, 6 are tilted so that the outer peripheral surfaces 7a, 7a of the power rollers 7, 7 contact with the closer-to-outer-periphery part of the input-side concave surface 2a and with the closer-to-center part of the output-side concave surface 4a. Tilt angles of the displacement shafts 6, 6 are set intermediate between those illustrated in FIGS. 3A and 3B, thereby obtaining an intermediate transmission gear ratio between the input shaft 1 and the output shaft 3.

For enhancing the driving force transmittable by the above-mentioned toroidal type continuously variable transmission, it has hitherto been preferable to increase contact surface pressures on contact areas through which the power is transmitted, i.e., the contact areas between the input-side concave surface 2a and the outer peripheral surface 7a, 7a of the power rollers 7, 7 in the case of the toroidal type continuously variable transmission illustrated in, e.g., FIGS. 3A and 3B.

When simply increasing the contact surface pressure on each contact surface area, however, a decrease in the life-span of rolling fatigue occurs in the contact surface areas due to a repetitive stress applied onto the rolling surface. Also, there arises a problem in which a loss in the power transmission on each contact surface area increases. This leads to an increase in the power required for rotating the input-side disk 2.

SUMMARY OF THE INVENTION

It is a primary object of the present invention to provide a power transmission device such as a toroidal type continuously variable transmission or the like that is capable of transmitting large power without causing a decline of durability.

As in the case of a power transmission device such as the above-mentioned toroidal type continuously variable transmission, the power transmission device according to the present invention comprises driving members having driving surfaces and a driven member having a driven surface. The power is transmitted from the driving members to the driven member by causing relative displacements between the driving members and the driven member in a state where the driving surfaces are pressed against the driven surface.

Particularly, in the power transmission device of this invention, a traction coefficient $\mu$ expressed by a ratio T/N is maximized with respect to contact areas between the driving surface pressure on said contact areas on the assumption that T is the driving force transmitted from the driving members to the driven member, and N is the pressing force acting on the contact areas in perpendicular directions. The contact surface pressure is controlled based on a radius of curvature of at least one of, e.g., the outer peripheral surfaces 7a, 7a of the power rollers 7, 7, the input-side concave surface 2a and the output-side concave surface 4a.

The thus constructed power transmission device of this invention is capable of maximizing the driving force T obtained with respect to the pressing force N. In consequence, the maximum power can be transmitted while retaining the life-span of rolling fatigue.

3

BRIEF DESCRIPTION OF THE DRAWINGS

Other objects and advantages of the present invention will become apparent during the following discussion in conjunction with the accompanying drawings, in which.

DESCRIPTION OF THE PREFERRED EMBODIMENTS

Figure 1:
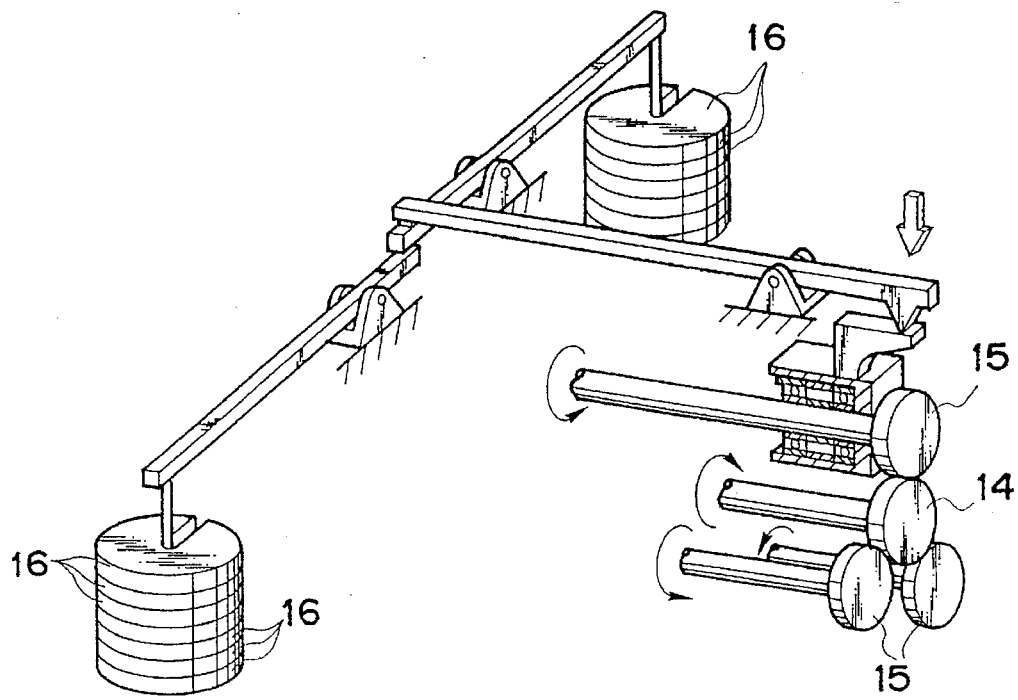
FIG. 1 is a perspective view illustrating a testing machine employed for a test.

FIG. 1 illustrates a Soda four-cylinder type fatigue friction testing machine employed for an experiment conducted in the course of completing the present invention. In this testing machine, three driving disks 15 are pressed against the outer peripheral surface of a sample disk 14. An accurate value of a traction coefficient $\mu$ between the sample disk 14 and the driving disks 15 is obtained. The upper driving disk 15 among the three driving disks 15 is pressed against the sample disk 14 by dint of weights of load bobs 16, 16. It is therefore possible to freely control a maximum contact surface pressure Pmax of contact areas between the outer peripheral surface of the sample disk 14 and the outer peripheral surfaces of the respective driving disks 15.

The present invention investigated a relationship between $\mu$ and Pmax (GPa) under the conditions as shown in the following Table by use of the above-mentioned fatigue friction testing machine. Results shown in FIG. 2 are consequently obtained.

TABLE

| | |
|---|---|
| Disk Diameter (mm) | 60 |
| Disk Width (mm) | 10 |
| Disk Generatrix Curvature | Sample Disk: 30 – ∞ (Flat) |
| Radius Rp (mm) | [4 Types] |
| | Driving Disk: ∞ (Flat) |
| Disk Material | Hardened Steel |
| Disk Surface Hardness ($H_RC$) | 60–64 |
| Disk Surface Roughness (μmRa) | 0.09–0.10 |
| Maximum Contact Pressure Pmax (GPa) | 0.6–2.9 |
| Rolling Speed V (m/s) | 7.8–15.7 |
| Slip Ratio S (%) | 0.55–2.2 |
| Sample Oil | Traction Oil |

Figure 2:
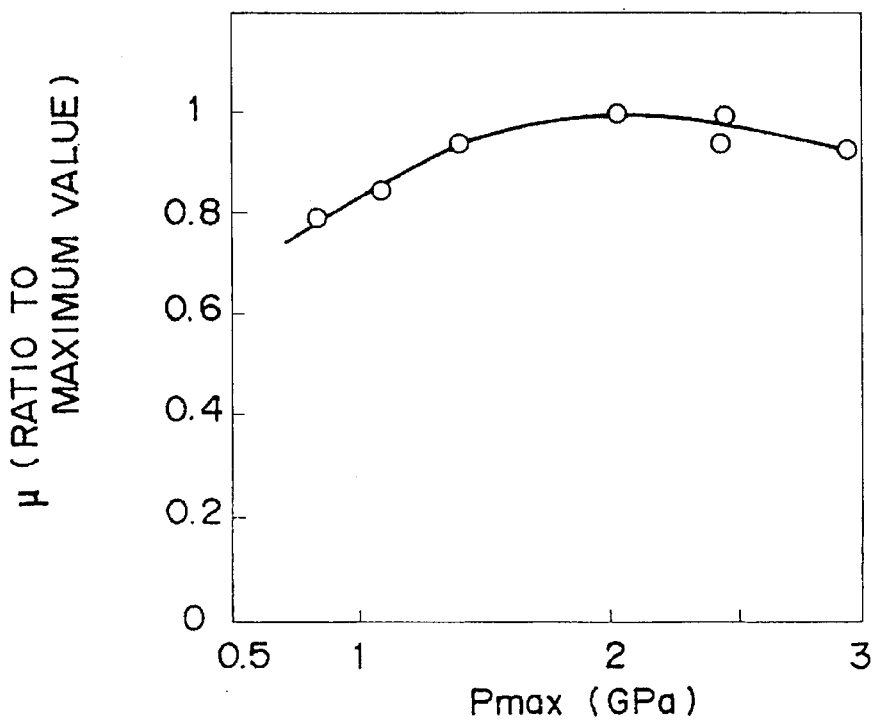
FIG. 2 is a graphic chart showing a relationship between $\mu$ and Pmax that are obtained as a result of the test.

As is evident from FIG. 2, the traction coefficient $\mu$ does not simply increase with an increment in Pmax. Namely, the traction coefficient $\mu$ gradually increases until Pmax reaches a certain range. When Pmax reaches the certain range the traction coefficient $\mu$ remains near the maximum value and does not substantially change. Further, when Pmax increases beyond this range, the traction coefficient $\mu$ decreases.

For instance, when the test is conducted under the conditions shown in the above-mentioned Table, the traction coefficient $\mu$ rapidly increases with the increment in Pmax in a range of Pmax$\leq$1.0 GPa. When Pmax>1.0 GPa, however, an increasing rate of $\mu$ decreases. The traction coefficient $\mu$ comes to the maximum value in a range defined such as Pmax=1.7–2.0 GPa. Further, when Pmax>2.0 GPa, the traction coefficient $\mu$ gradually decreases. The traction coefficient $\mu$ is reduced down to 89% of the maximum value around Pmax=2.9 GPa.

Note that the slip ratio S and the rolling speed V shown in the Table are set to fixed values when preparing FIG. 2.

Incidentally, the tests were performed with a different combination of the slip ratio S and the rolling speed V, yet the tendency remains unchanged from that shown in FIG. 2.

Heretofore, it had been believed that the traction coefficient $\mu$ increases with the increment in Pmax. The present inventors have contemplated the reason why the results are obtained as shown in FIG. 2 on the basis of the following items (1) and (2).

(1) The results are based on a rheology behavior of oil under a high surface pressure.

In the case of the power transmission device such as a toroidal type continuously variable transmission for transmitting the power through the oil on which the high surface pressure is applied, there exists a possibility in which the oil behavior does not satisfy the assumption of the conventional theory. For example, the assumption of the conventional theory may not be met because of deviations, due to temperature and pressure, from expected characteristics of an oil viscosity—pressure coefficient $\alpha$, and a reduction in the value of $\mu$max due to a spread of a heat zone toward a low S-side in a $\mu$-S curve that is derived from a heat emission of shearing of an oil film. Then, if the value of Pmax increases beyond a certain range, the traction coefficient $\mu$ decreases with this increase.

(2) The results are based on the traction conditions within the contact surfaces.

In the case of the power transmission device for transmitting the power through the oil on which the high surface pressure is applied, it is assumed that a rupture of the oil film exists partially in an elastic fluid lubricating area. In such a lubricating area, there is a possibility in which the traction is to be retained depending on not only a shearing stress of the oil but also a direct contact between the protruded portions of a rough surface. In such a case, the traction is determined in accordance with an unstable factor termed a projection-to-projection interference depending on variations in the lubricating state. Hence, the traction coefficient $\mu$ does not necessarily increase even when the formation of the oil film changes in degree due to the increment in Pmax.

In any case, as shown above, the traction coefficient $\mu$ does not simply increase with the increment in Pmax. Rather, the traction coefficient $\mu$ reaches the maximum value when Pmax reaches a certain value. The traction coefficient $\mu$ is reduced with a further increment in Pmax. It will thus be appreciated that in designing a power transmission device for transmitting large power, if the maximum contact surface pressure Pmax is increased based on the conventionally known theory, a result is obtained which is actually contrary to that theory. That is, the traction coefficient $\mu$ is reduced, whereby a large power cannot be transmitted. Furthermore, it is known that the life-span of rolling fatigue is inversely proportional to substantially the 7th through 9th powers of Pmax. Accordingly, increasing Pmax based on the conventionally known theory also shortens the life-span of rolling fatigue of the driving surface.

That is, it is known that the life-span of rolling fatigue is inversely proportional to substantially the seventh through ninth power of Pmax. Hence, the increase in the traction coefficient $\mu$ can not be expected, yet it is not preferable to increase Pmax.

In contrast with this, according to the power transmission device of this invention, Pmax is controlled so that the traction coefficient $\mu$ becomes the maximum value. Accordingly, it is possible to attain the power transmission device capable of transmitting the large power while limiting a reduction in the life-span of rolling fatigue. When viewed from a different aspect, in the power transmission device for transmitting a predetermined driving force T (=μN), μ is maximized, whereas N is minimized. The power transmission device having a long life-span of rolling fatigue can be thereby constructed.

Figure 3A:
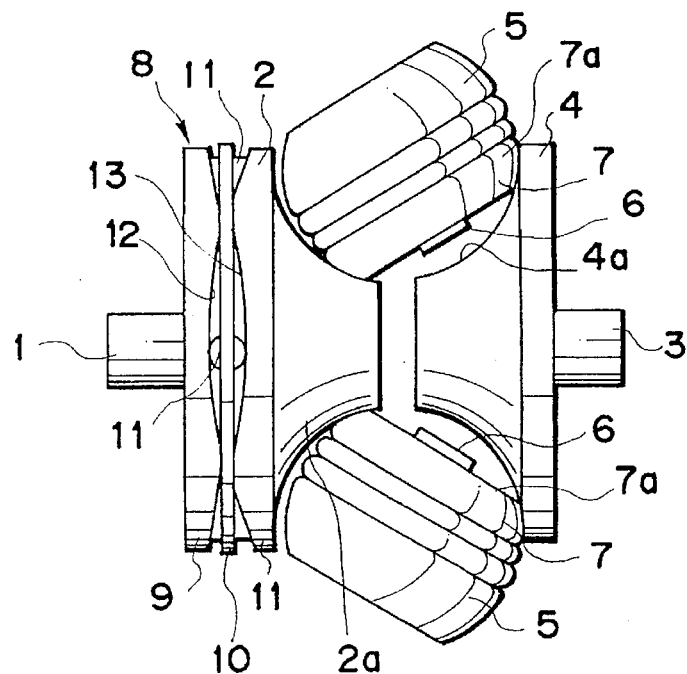
FIGS. 3A and 3B are sectional views illustrating a toroidal type continuously variable transmission to which the present invention is applied when accelerated and decelerated.
Figure 3B:
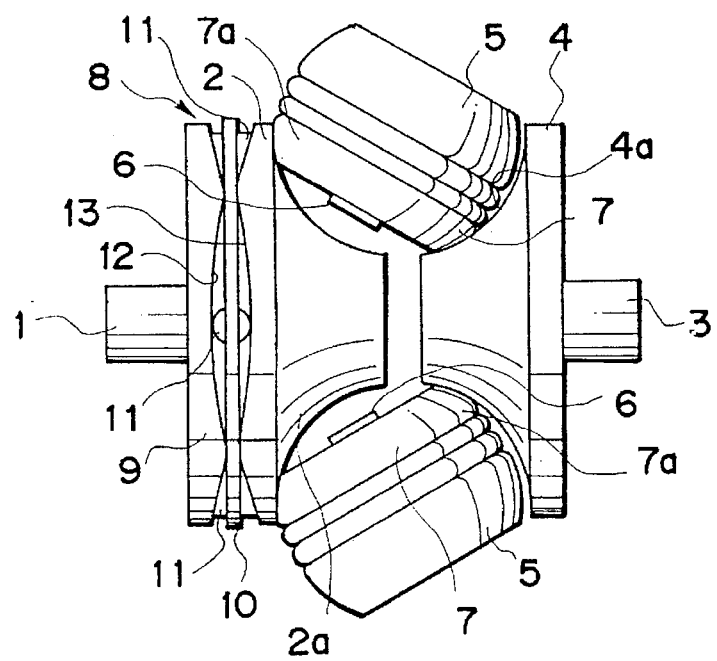

Note that the power transmission device according to this invention is utilizable for transmitting the power on the basis of the rolling contact. The same power transmission device is not limited to the toroidal type continuously variable transmission as shown in FIGS. 3A and 3B but may be applied to other types of transmissions and further to mechanical parts such as a cam follower or the like, ball screws, rolling bearings, linear guides and so forth.

Moreover, when tested under the conditions shown in the Table given above, the traction coefficient μ comes to the maximum value in the range of 1.7–2.0 Gpa. The maximum value of μ is, however, variable depending on a type, dimensional parameters and a configuration of the power transmission device to which the present invention is applied, as well a temperature and speed employed and other operating conditions. Nonetheless, it is possible to construct a power transmission device which is capable of transmitting large power by obtaining Pmax with μ being maximized from the test, and which also exhibits a long life-span of rolling fatigue.

The power transmission device according to the present invention is constructed and acts as discussed above. The power transmission device is therefore capable of transmitting the large power while maintaining durability.

It is apparent that, in this invention, a wide range of different working modes can be formed based on the invention without deviating from the spirit and scope of the invention. This invention is not restricted by its specific working modes except being limited by the appended claims.

What is claimed is:

1. A method of transmitting power in a power transmission device including a driving member having a driving surface and a driven member having a driven surface, said driving surface and said driven surface having juxtaposed contact areas for performing a power transmission from said driving member to said driven member by relative displacement of said driving surface and said driven surface, said method comprising the following steps:

determining, as a function of contact surface pressure on said contact areas, a traction coefficient μ expressed as a ratio T/N for a predetermined driving speed and a predetermined slip coefficient of said driving surface and said driven surface, where T is a driving force transmitted from said driving member to said driven member and N is a pressing force acting on said contact areas in a direction perpendicular to said contact areas;

from results of said determining step, obtaining a contact surface pressure at which the traction coefficient μ is maximized and beyond which the traction coefficient μ decreases; and based on results of said obtaining step, controlling the contact surface pressure on said contact areas such that the traction coefficient μ is maximized.

\* \* \* \* \*